United States Patent [19]

Hall et al.

[11] Patent Number: 5,280,034
[45] Date of Patent: Jan. 18, 1994

[54] BIS-HETEROCYCLIC PROSTAGLANDIN ANALOGS

[75] Inventors: Steven E. Hall, Pennington; Philip M. Sher, Plainsboro, both of N.J.

[73] Assignee: E. R. Squibb & Sons, Inc., Princeton, N.J.

[21] Appl. No.: 749,395

[22] Filed: Aug. 23, 1991

[51] Int. Cl.$^5$ .................. A61K 31/42; A61K 31/415; C07D 233/60; C07D 263/32
[52] U.S. Cl. .................................... 514/374; 514/397; 514/400; 548/236; 548/313.4; 548/333.5
[58] Field of Search ............ 548/236, 336, 343, 313.4, 548/333.5; 514/374, 397, 400

[56] References Cited

U.S. PATENT DOCUMENTS

| | | | |
|---|---|---|---|
| 4,258,058 | 3/1981 | Witte et al. | 424/309 |
| 4,416,896 | 11/1983 | Nakane et al. | 424/285 |
| 4,418,076 | 11/1983 | Nakane et al. | 424/285 |
| 4,443,477 | 4/1984 | Witte et al. | 424/319 |
| 4,463,015 | 7/1984 | Haslanger et al. | 424/285 |
| 4,474,804 | 10/1984 | Das et al. | 424/285 |
| 4,522,949 | 6/1985 | Das et al. | 514/469 |
| 4,536,513 | 8/1985 | Das et al. | 514/469 |
| 4,752,613 | 6/1988 | Floyd et al. | 514/438 |
| 4,752,616 | 6/1988 | Hall et al. | 514/510 |
| 4,783,473 | 11/1988 | Hall et al. | 514/382 |
| 4,965,279 | 10/1990 | Misra et al. | 514/381 |
| 4,975,452 | 12/1990 | Sher et al. | 514/438 |

FOREIGN PATENT DOCUMENTS

| | | | |
|---|---|---|---|
| 0194548 | 3/1986 | European Pat. Off. | 514/438 |
| 0374952 | 12/1988 | European Pat. Off. | 548/200 |

*Primary Examiner*—Mary C. Lee
*Assistant Examiner*—Joseph K. McKane
*Attorney, Agent, or Firm*—John M. Kilcoyne

[57] ABSTRACT

Thromboxane receptor antagonist activity is exhibited by compounds of the formula

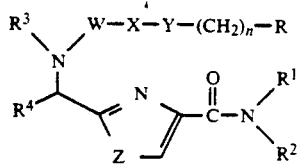

wherein:
W is —$(CH_2)_m$— or

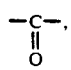

but if $R^3$ and $R^4$ complete an aromatic ring, then W cannot be

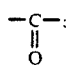

X is —$(CH_2)_2$—, —CH=CH— or phenylene;
Y is —O—, a single bond or vinylene, except that Y cannot be —O— when n is 0, and if Y is vinylene, then n must be 0;
Z is O or NH;
$R^3$ and $R^4$ are each independently hydrogen, alkyl, alkenyl, or alkynyl, or $R^3$ and $R^4$ together complete a ring as defined in the specification, optionally substituted through a ring carbon with an oxo or hydroxyl group; and the remaining symbols are as defined in the specification.

14 Claims, No Drawings

BIS-HETEROCYCLIC PROSTAGLANDIN ANALOGS

FIELD OF THE INVENTION

This invention relates to bis-heterocyclic prostaglandin analogs useful as thromboxane $A_2$ receptor antagonists.

BRIEF DESCRIPTION OF THE INVENTION

A compound of the formula

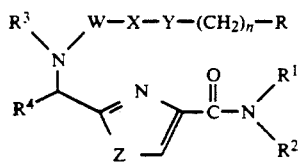

is a thromboxane $A_2$ ($TXA_2$) receptor antagonist or a combined thromboxane $A_2$ receptor antagonist/thromboxane synthetase inhibitor. Compound I is useful, for example, in treating thrombotic or vasospastic disease. In compound I and throughout this specification, the symbols above are defined as follows:

W is $-(CH_2)_m-$ or

but if $R^3$ and $R^4$ complete an aromatic ring, then W cannot be

X is $-(CH_2)_2-$, $-CH=CH-$ or phenylene;
Y is $-O-$, a single bond or vinylene, except that Y cannot be $-O-$ when n is 0, and if Y is vinylene, then n must be 0;
Z is O or NH;
m is 1, 2, or 3;
n is 0, 1, 2 or 3;
R is $CO_2H$, $CO_2$alkyl, $CO_2$alkali metal, $CH_2OH$, $CONHSO_2R^5$, $CONHR^6$, or $-CH_2$-5-tetrazolyl;
$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide

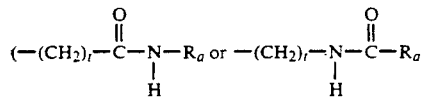

wherein t is 1 to 12 and $R_a$ is alkyl, aryl, cycloalkyl, or cycloalkylalkyl), each of $R^1$ being unsubstituted or optionally substituted with alkyl, aryl, cycloalkyl, or cycloalkylalkyl;
$R^2$ is hydrogen, alkyl, aryl, or aralkyl; or
$R^1$ and $R^2$ together with the nitrogen to which they are linked form a 5- to 8-membered ring;
$R^3$ and $R^4$ are each independently hydrogen, alkyl, alkenyl, or alkynyl; or $R^3$ and $R^4$ together complete a pyrrolyl, pyrrolidinyl, imidazolyl, imidazolinyl, pyrazolyl, pyrazolinyl, pyrazolidinyl, dihydropyridyl, tetrahydropyridyl, piperidyl, dihydropyrazinyl, tetrahydropyrazinyl, piperazinyl, dihydropyrimidinyl, tetrahydropyrimidinyl, hexahydropyrimidinyl, dihydropyridazinyl, tetrahydropyridazinyl, hexahydropyridazinyl, indolyl, dihydroindolyl, tetrahydroindolyl, hexahydroindolyl, octahydroindolyl, isoindolyl, dihydroisoindolyl, tetrahydroisoindolyl, hexahydroisoindolyl, octahydroisoindolyl, purinyl, dihydropurinyl, tetrahydropurinyl, hexahydropurinyl, octahydropurinyl, dihydroquinolyl, tetrahydroquinolyl, hexahydroquinolyl, octahydroquinolyl, decahydroquinolyl, dihydrophthalizinyl, tetrahydrophthalizinyl, hexahydrophthalizinyl, octahydrophthalizinyl, decahydrophthalizinyl, dihydronaphthyridinyl, tetrahydronaphthyridinyl, hexahydronaphthyridinyl, octahydronaphthyridinyl, decahydronaphthyridinyl, dihydroquinoxalinyl, tetrahydroquinoxalinyl, hexahydroquinoxalinyl, octahydroquinoxalinyl, decahydroquinoxalinyl, dihydroquinazolinyl, tetrahydroquinazolinyl, hexahydroquinazolinyl, octahydroquinazolinyl, decahydroquinazolinyl, triazolyl, triazolinyl, triazolidinyl, oxazinyl, dihydrooxazinyl, tetrahydrooxazinyl, isoxazinyl, dihydroisoxazinyl, tetrahydroisoxazinyl, morpholinyl, azepinyl, or diazepinyl ring, optionally substituted through a ring carbon atom with a halo, trifluoromethyl, oxo or hydroxyl group;
$R^5$ is alkyl, aryl or aralkyl; and
$R^6$ is hydrogen, alkyl, aryl, aryl or aralkyl.

Preferred compounds of formula I have the formula I(A)

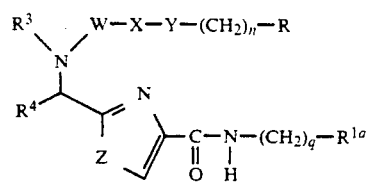

wherein q is an integer from 1 to 7 and $R^{1a}$ is cycloalkyl or aryl. It is also preferred that $R^3$ and $R^4$ complete a pyrrolidinyl or imidazolyl ring.

DETAILED DESCRIPTION OF THE INVENTION

Definition of Terms

The following definitions apply to the terms used throughout this specification, unless otherwise limited in specific instances.

The term "alkyl" includes both straight and branched chain radicals of up to 12 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof and the like, which may be substituted with one or two trifluoromethyl, halo or hydroxyl groups.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl.

The term "aryl" or "Ar" refers to monocyclic or bicyclic aromatic groups containing from 6 to 10 carbons in the ring portion, such as phenyl and naphthyl, which may include 1 or 2 substituents on either the phenyl or naphthyl such as alkyl, trifluoromethyl, halogen (Cl, Br, I or F), alkoxy, phenylalkoxy, hydroxy, alkylthio, alkylsulfinyl, alkylsulfonyl, phenylthio, phenylsulfinyl and/or phenylsulfonyl.

The term "aralkyl" refers to alkyl groups as discussed above having an aryl substituent, such as benzyl.

The terms "alkoxy" and "aralkoxy" refer to the above alkyl and aralkyl groups linked to an oxygen atom.

The term "alkanoyl" refers to the above alkyl groups linked to a carbonyl group.

The term "halogen" or "halo" refers to chlorine, bromine, fluorine or iodine, with chlorine being preferred.

The term "alkenyl" as employed herein refers to carbon chains of 2 to 12 carbons, preferably 3 to 10 carbons, having at least one double bond. With respect to the $R^1$ substituent, the alkenyl group will be separated from "N" by at least one saturated carbon moiety such as $-(CH_2)_q-$ wherein q can be 1 to 14, such as 2-propenyl, 2-butenyl, 3-butenyl, 2-pentenyl, 4-pentenyl and the like, and may include a halogen substituent such as I, Cl, or F.

The term "alkynyl" as employed herein refers to carbon chains of 2 to 16 carbons, preferably 3 to 10 carbons, having at least one triple bond. With respect to the $R^1$ substituent, the alkynyl group will be separated from "N" by at least one saturated carbon moiety such as $-(CH_2)_q-$ wherein q can be 1 to 14, such as 2-propynyl, 2-butynyl, 3-butynyl and the like.

The term "cycloheteroalkyl" as used herein as an $R^1$ substituent refers to 5-, 6- or 7-membered saturated rings that include 1 or 2 heteroatoms such as nitrogen, oxygen and/or sulfur, and which are linked to the "N" of the

group through a carbon atom either beta or gamma to a heteroatom, such as

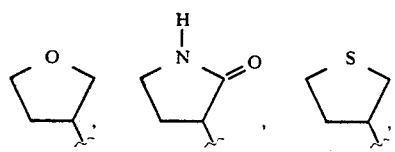

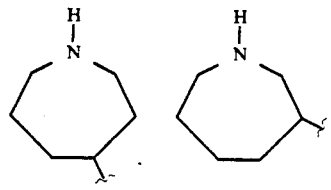

and the like.

The term "heteroaryl" or "heteroaromatic" as an $R^1$ substituent refers to 5- or 6-membered aromatic rings that include 1 or 2 heteroatoms such as nitrogen, oxygen or sulfur, which are not directly linked through a heteroatom to the "N" of the

group, such as

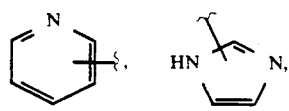

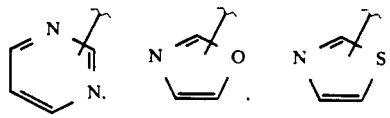

and the like.

The term "cycloheteroalkylalkyl" as used herein with respect to $R^1$ refers to 5-, 6- or 7-membered saturated rings that include 1 or 2 heteroatoms such as nitrogen, oxygen or sulfur, and are linked to the "N" of the

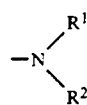

group through a $(CH_2)_x$ chain wherein x is 1 to 12, preferably 1 to 8, such as

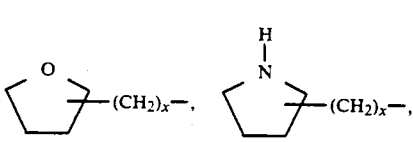

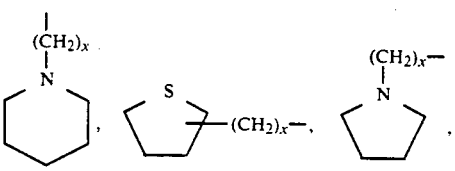

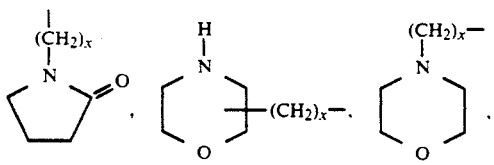

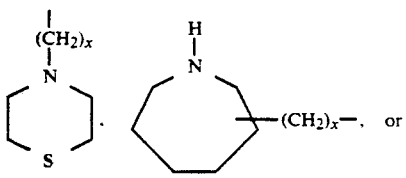

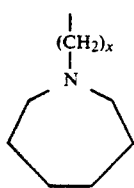

and the like.

The term "heteroarylalkyl" as used herein with respect to $R^1$ refers to 5-, 6- or 7-membered aromatic rings that include 1 to 4 nitrogen and/or 1 or 2 oxygen or sulfur atoms, and is linked to the "N" of the

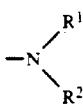

group through a $-(CH_2)_x-$ chain where x is 1 to 12, preferably 1 to 8, such as

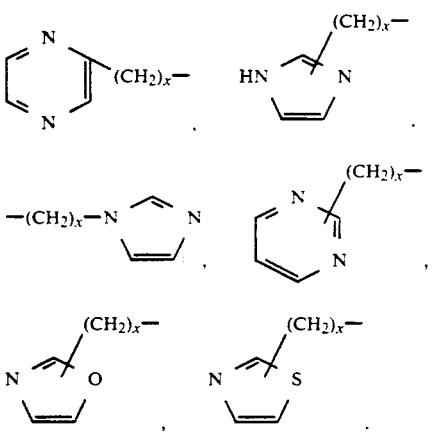

Compounds of the present invention may be prepared as follows.

An acid of the formula

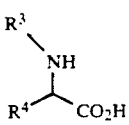

is reacted with t-butyl alcohol in an organic solvent such as dimethylformamide (DMF) in the presence of a coupling reagent such as 1-(3-dimethylaminopropyl)-3-ethylcarbodiimide hydrochloride (WSC) or dicyclohexylcarbodiimide (DCC), optionally a catalyst such as 1-hydroxybenzotriazole (HOBt), and an amine base such as dimethylaminopyridine (DMAP) at about 20° to 30° C. to form an ester

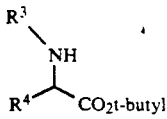   III

Ester III reacts with a haloester IV $$halo-W-X-Y-(CH_2)_n-CO_2alkyl$$

(wherein halo is preferred to be bromo) by treatment with a condensing catalyst (e.g., sodium hydride) in an organic solvent such as tetrahydrofuran (THF) at about $-78°$ C. in an inert atmosphere (e.g., argon) to form a diester

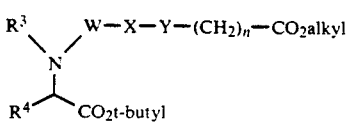   V

Diester V is de-esterified by treatment with an acid (e.g., hydrochloric acid) in an organic solvent (e.g., dioxane) to form an acid-ester

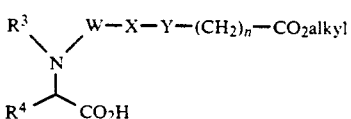   VI

Acid-ester VI is reacted with an amine hydrochloride salt

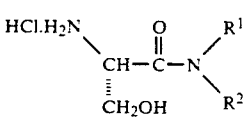   VII in an organic solvent (e.g., DMF) in the presence of a catalyst (e.g., HOBt monohydrate), a coupling reagent (e.g., WSC) and an amine base (e.g., triethylamine) at about 20° to 30° C. to form an amide-ester

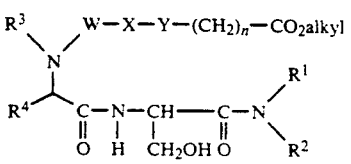   VIII as well as a related olefin wherein one of the bonds in $-(CH_2)_n-$ is replaced by a double bond. This olefin may be conventionally hydrogenated in the presence of a catalyst (e.g., 10% palladium on activated carbon) in an inert solvent (e.g., methanol) under a hydrogen atmosphere at about 20° to 30° C. to form amide-ester VIII.

Amide-ester VIII undergoes cyclodehydration by treatment with an amine base (e.g., triethylamine) and a sulfonyl halide (e.g., mesyl chloride) in an inert organic solvent (e.g., methylene chloride) at about 0° to 30° C., followed by an alkali metal hydroxide, bicarbonate or carbonate (e.g., potassium carbonate) in an inert solvent (e.g., acetone) at about 20° to 30° C. to form an oxazoline

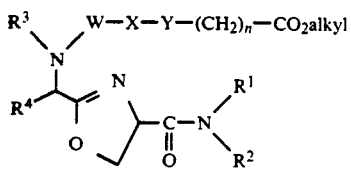   IX

Oxazoline IX is treated with an oxidizing agent such as cupric bromide in the presence of 1,8-diazabicyclo[5.4.0]undec-7-ene (DBU) in an inert organic solvent (e.g., ethyl acetate/chloroform) under an inert atmosphere (e.g., argon) at about 20° to 30 ° C. to form compound I, wherein R is CO₂alkyl.

Alternatively, compound I is prepared from a nitrogen-protected acid

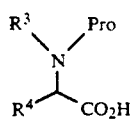   X wherein Pro is a nitrogen-protecting group such as benzyloxycarbonyl. Acid X is reacted with amine hydrochloride salt VII by treatment with a coupling reagent (e.g., WSC), a catalyst (e.g., HOBt) and an amine base (e.g. triethylamine) in an organic solvent (e.g., DMF) at about 20° to 30° C. to form an amide

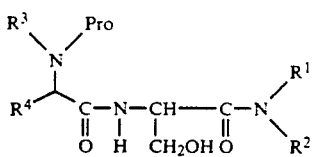   XI

Amide XI undergoes cyclodehydration and oxidation as described for compounds VIII→IX→I to form an oxazole

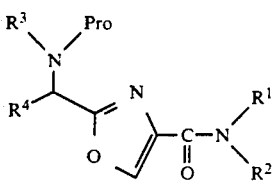   XII

Oxazole XII is deprotected (e.9., with H₂) in an inert solvent (e.g., methanol) in the presence of a catalyst (e.g., 10% palladium on activated carbon) to form an unprotected oxazole

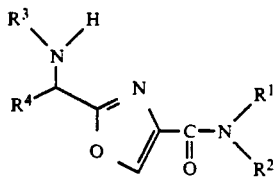   XIII

Oxazole XIII is reacted with haloester IV as described for compound III→V to form compound I. Alternatively, oxazole XIII is reacted with an aldehyde-ester

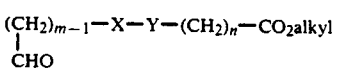   XIV followed by treatment with a reducing agent (e.g., sodium cyanoborohydride) in an inert solvent (e.g., methanol) under an inert atmosphere (e.g., argon) at about 20° to 30° C. to form compound I. In a further alternative, an acid of the formula XV

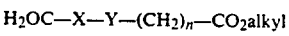

is treated with oxalyl chloride to form an acid-chloride XVI

Oxazole XIII reacts with acid halide XVI and an amine base (e.g., triethylamine) in an inert solvent (e.g., methylene chloride) in an inert atmosphere (e.g., argon) at about −5° to 5° C. to form compound I wherein W is —C(O)—.

A further alternative is useful, inter alia, for compounds wherein R³ and R⁴ complete a ring substituted with oxo at the carbon atom adjacent to the ring nitrogen atom. Amine hydrochloride VII is reacted with an amino acid

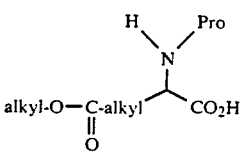   XVII by treatment with an amine base (e.g., 4-methylmorpholine), a coupling reagent (e.g., WSC), a catalyst (e.g., HOBt) in an inert solvent (e.g., DMF) in an inert atmosphere (e.g., argon) at about 20° to 30° C. to form a diamide

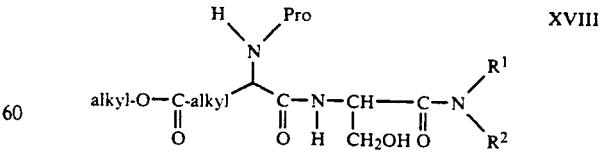   XVIII

Diamide XVIII undergoes cyclodehydration by treatment with, for example, triphenylphosphine, diisopropylethylamine and carbon tetrachloride in an inert solvent or solvent mixture (e.g., methylene chloride and acetonitrile) under an inert atmosphere (e.g., argon) at about 0° to 15° C. to form an oxazoline

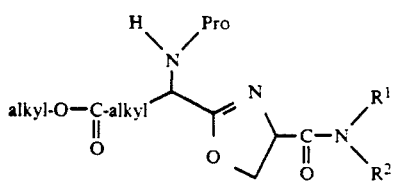

Oxazoline XIX is oxidized as described for oxazoline IX to form an oxazole

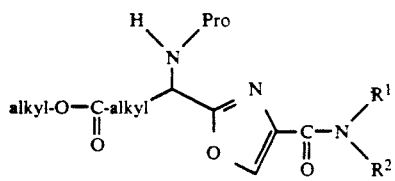

Oxazole XX is deprotected and then reacted with aldehyde-ester XIV as described for compounds XII→XIII→I to form compound I wherein $R^3$ and $R^4$ are each independently hydrogen, alkyl, or aralkyl. Alternatively, when $R^9$ comprises alkoxycarbonylalkyl, treatment with a deprotecting agent (e.g., trifluoroacetic acid when alkoxycarbonyl is t-butoxycarbonyl) in an inert solvent (e.g., methylene chloride) in an inert atmosphere (e.g., argon) at about $-10°$ to $10°$ C. forms compound I wherein $R^3$ and $R^4$ comprise a ring substituted with oxo.

In a further alternative, compound I wherein $R^3$ and $R^4$ comprise a ring substituted with a hydroxyl group may be prepared as follows. A nitrogen-protected ester

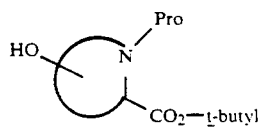

(wherein the ring is as defined by $R^3$ and $R^4$) is treated with a protecting agent (e.g., thexyldimethylsilyl chloride), a coupling agent (e.g., DMAP) and an amine base (e.g., triethylamine) in an inert solvent (e.g., methylene chloride) at about 20° to 30° C. to form a doubly protected ester

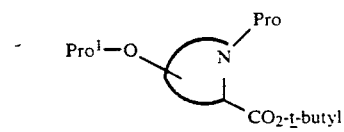

wherein $Pro^1$ is an oxygen-protecting group such as benzyl, methoxymethyl, or preferably a silyl-protecting group, such as

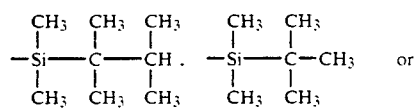

(dimethylthexylsilyl)   (dimethyl-t-butylsilyl)

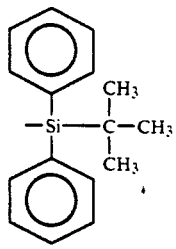

(diphenyl-t-butylsilyl)

(t-butylchlorodiphenylsilane) and the like.

Doubly-protected ester XXII reacts with amine hydrochloride VII as described for compounds VI→VIII, then undergoes cyclodehydration and oxidation as described for compounds VIII→IX→I to form a doubly-protected oxazole

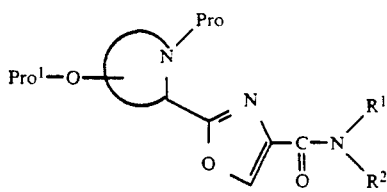

Doubly-protected oxazole XXIII is treated with a deprotecting agent (e.g., tribromoborane) in an inert solvent (e.g., methylene chloride) in an inert atmosphere (e.g., argon) at about $-10°$ to $10°$ C., followed by an acid (e.g., hydrochloric acid) to form an amine hydrochloride-oxazole

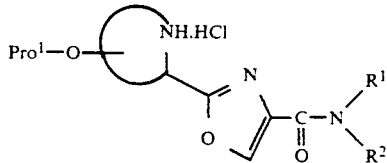

Amine hydrochloride oxazole XXIV reacts with aldehyde-ester XIV as described previously herein or with acid-ester XV in an organic solvent (e.g., DMF) in the presence of an amine base (e.g., 4-methylmorpholine), a coupling agent (e.g., WSC) and a catalyst (e.g., HOBt) at about 20° to 30° C. to form an oxygen-protected ester

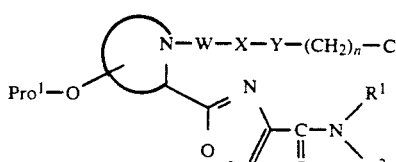

Ester XXV is treated with a deprotecting agent (e.g., tetrabutylammonium fluoride) in an inert solvent (e.g., THF) in an inert atmosphere (e.g., argon) at about 20° to 30° C. to form compound I wherein $R^3$ and $R^4$ complete a ring substituted with hydroxyl.

Alternatively, when Z is NH, acid X undergoes a coupling reaction with an amine

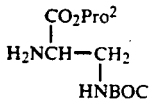
XXVI (wherein BOC is t-butoxycarbonyl and Pro² is an oxygen protecting group as defined by Pro¹, wherein Pro² may be selectively removed in the presence of Pro) in the presence of a coupling agent such as WSC and HOBt in methylene chloride for about 12 to 90 hours, employing an acid:amine molar ratio of about 1.2:1 to about 1:1. The resulting amide undergoes a thionation reaction with Lawesson's reagent in the presence of benzene at about 50° to 65° C. for about 1 to 4 hours to form an ester

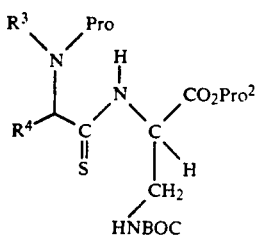
XXVII

Ester XXVII is cyclized in an inert solvent (e.g., acetonitrile, methylene chloride or THF) with triphenylphosphine in an ester:triphenylphosphine molar ratio of about 0.8:1 to 1:1, along with carbon tetrachloride in the presence of an amine base (e.g., triethylamine or diisopropylethylamine) to form an imidazoline

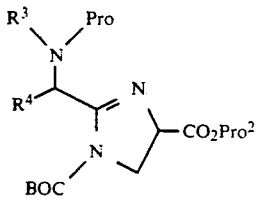
XXVIII

Imidazoline XXVIII is then deprotected to remove the Pro² protecting group using conventional procedures (e.g., hydrogenation when Pro² is benzyl) to form an acid

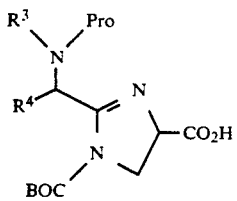
XXIX

Next, acid XXIX is coupled with an amine

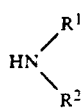
XXX in the presence of an amine base (e.g., pyridine or triethylamine) under an inert atmosphere (e.g., argon) in the presence of a coupling agent such as WSC and HOBT in an inert solvent such as chloroform, employing a molar ratio of about 0.8:1 to 1.2:1 to form an amide

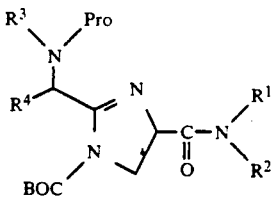
XXXI

Carbonylamine XXXI is then treated with a deprotecting agent (e.g., trifluoroacetic acid) in an inert solvent (e.g., methylene chloride) to remove the BOC group and form an imidazoline of the formula

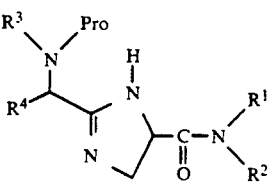
XXXII

Imidazoline XXXII is treated with an oxidizing agent (e.g., manganese dioxide) in an inert solvent (e.g., chloroform) to form an imidazole

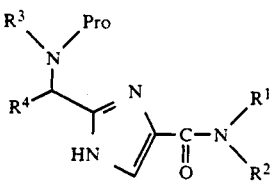
XXXIII

Imidazole XXXIII is treated as described for compounds XII→XIII→I or XX→I to form compound I wherein Z is NH.

Compounds of formula I wherein X is —(CH$_2$)$_2$— may be prepared from the corresponding acids wherein X is —CH=CH— by hydrogenation using, for example, a hydrogenation catalyst (e.g., palladium on carbon) in an inert organic solvent (e.g., ethyl acetate or acetic acid).

Compounds of formula I wherein R is CO$_2$-alkali metal can be prepared from the corresponding esters by treating the ester with bases such as lithium hydroxide or potassium hydroxide. The corresponding acids (wherein R is CO$_2$H) are prepared by neutralizing the foregoing alkali metal salts with an acid (e.g., dilute hydrochloric acid or oxalic acid).

Compounds of the invention wherein R is CONHSO$_2$R$^5$ are prepared by treating the associated acids (wherein R is CO$_2$H) with a sulfonamide

XXXIV in the presence of a coupling agent (e.g., carbonyldiimidazole or WSC) in the presence of an amine (e.g., DMAP) under an inert atmosphere (e.g., argon).

Compounds of formula I wherein R is CONHR$^6$ wherein R$^6$ is other than hydrogen may be prepared from the corresponding acid by treatment with WSC in the presence of DMF, HOBt, an organic base (e.g., triethylamine) and an amine XXXV

HNHR⁶

Where $R^6$ in compound I is hydrogen, ammonium chloride is used in place of amine XXXIV.

USE AND UTILITY

The compounds of this invention are thromboxane receptor antagonists and as such are useful as inhibitors of thromboxane receptor mediated actions. The term "thromboxane receptor antagonist" includes compounds that are so-called thromboxane $A_2$ receptor antagonists, thromboxane $A_2$ antagonists, thromboxane $A_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds; for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogenstreptokinase activator complex (APSAC) within 6 hours of a myocardial infarction. In such case, the thrombolytic agent may be used in amounts conventionally employed, for example, as disclosed in the Physicians' Desk Reference, for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight of compound I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

PREFERRED EMBODIMENTS

The following examples represent preferred embodiments of the present invention. Unless otherwise indicated, all temperatures are expressed in degrees Celsius.

EXAMPLE 1

2-[[2-[4-[[(4-Cyclohexylbutyl)amino]carbonyl-2-oxazolyl]-1-pyrrolidinyl]methyl]benzenepropanoic acid A. N-(4-Cyclohexylbutyl)-2-aminoacetamide, monohydrochloride To a stirred solution of 1.14 g (6.5 mmol) of t-butyloxycarbonylglycine in 10 mL of tetrahydrofuran at 0° C. was added 1.05 g (6.5 mmol) of carbonyldiimidazole. The ice bath was removed and the reaction mixture was allowed to warm to room temperature over a period of 90 minutes. To this mixture was added 1.18 g (6.14 mmol) of 4-cyclohexylbutylamine hydrochloride followed by 1.0 mL of triethylamine (7.2 mmol). An exotherm was noted which was accompanied by the formation of a thick precipitate. An additional 5.0 mL of tetrahydrofuran was added and the reaction mixture was allowed to stir at room temperature for 18.5 hours. The reaction mixture was diluted with 30 mL of water, acidified to pH 4 with 1N hydrochloric acid, and extracted with two 30 mL portions of ethyl acetate. The combined ethyl acetate extracts were washed with 30 mL of 0.1N sodium hydroxide, dried (magnesium sulfate), filtered and concentrated in vacuo to afford 1.97 g of crude amide. To a flask containing the above amide was added 20 mL of pre-chilled (0° C.) trifluoroacetic acid. After stirring at 0° C. for 30 minutes, the reaction mixture was concentrated in vacuo at 0° C. The residue was reconcentrated from 25 mL of toluene. The residue was dissolved in 25 mL of methanol and treated with approximately 1 mL of concentrated hydrochloric acid. This was concentrated in vacuo, redissolved in methanol, and reconcentrated to afford a viscous oil. This was triturated in 50 mL of ether to afford 1.38 g of the title compound (84% overall).

B.
2-[[[2-[(4-Cyclohexylbutyl)amino]-1-(hydroxymethyl)-2-oxoethyl]amino]carbonyl]-1-pyrrolidinecarboxylic acid, phenylmethyl ester To a stirred mixture of N-benzyloxycarbonyl(D,L)-proline (2.50 g, 10.0 mmol), 1-hydroxybenzotriazole monohydrate (1.70 g, 10.0 mmol) and amine hydrochloride salt A (2.80 g, 10.0 mmol) in 150 mL of dimethylformamide was added triethylamine (4.20 mL, 30.0 mmol) and ethyl-3-(3-dimethylamino)propylcarbodiimide hydrochloride salt (1.92 g, 10.0 mmol) sequentially. This mixture was stirred at room temperature for 17 hours and concentrated in vacuo. The mixture was partitioned between 400 mL of ethyl acetate and 1N hydrochloric acid solution (2×50 mL), 0.2N sodium hydroxide solution (2×50 mL), saturated sodium bicarbonate solution (1×50 mL) and brine (1×100 mL). The organic layer was dried (magnesium sulfate), filtered and concentrated in vacuo. This layer was then chromatographed on 180 g of Merck silica gel 60 using 2% methanol/dichloromethane as eluant to give 4.10 g (86%) of amide B.

TLC: silica gel, 2% methanol/dichloromethane $R_f$ 0.26, cerium sulfate dip.

$^{13}$C of 3 (CDCl$_3$, 67.5 MHz) δ: 170.1, 136.3, 136.1, 128.4, 128.0, 127.7, 67.4, 67.2, 62.5, 62.3, 61.0, 54.6, 47.1, 39.9, 37.4, 37.0, 33.3, 29.5, 26.6, 26.3, 24.0.

C.
2-[4-[[(4-Cyclohexylbutyl)amino]carbonyl-4,5-dihydro-2-oxazolyl]-1-pyrrolidinecarboxylic acid, phenylmethyl ester To a stirred mixture of amide B (4.10 g, 8.67 mmol) and triethylamine (2.42 mL, 17.3 mmol) in 150 mL of dry dichloromethane under argon at 0° C. was added mesyl chloride (0.81 mL, 10.4 mmol). The mixture was stirred at 0° C. for 15 min and at room temperature for 35 min. The mixture was concentrated in vacuo. The residue was diluted with 100 mL of acetone and combined with potassium carbonate (4.79 g, 34.7 mmol). The mixture was refluxed for 1.5 hours and cooled to room temperature. The solid was filtered off and rinsed with acetone (4×40 mL). The filtrate was concentrated in vacuo and chromatographed on 220 g of Merck silica gel 60 using 2% methanol/dichloromethane as eluant to give 3.77 g (96%) of oxazoline C.

TLC: silica gel, 4% methanol/dichloromethane $R_f$ 0.54, cerium sulfate dip.

$^{13}$C of 4 (CDCl$_3$, 67.5 MHz) δ: 171.7, 171.5, 170.2, 167.2, 155.1, 154.6, 136.5, 136.1, 128.5, 128.4, 127.9, 127.6, 127.5, 72.4, 71.7, 68.3, 66.9, 55.0, 54.9, 52.0, 46.5, 39.3, 39.2, 37.4, 37.0, 33.2, 29.9, 29.5, 29.4, 26.6, 26.3, 24.0.

D.
2-[4-[[(4-Cyclohexylbutyl)amino]carbonyl]-2-oxazolyl]-1-pyrrolidinecarboxylic acid, phenylmethyl ester To a stirred mixture of cupric bromide (3.83 g, 17.2 mmol) and 1,8-diazabicyclo[5.4.0]undec-7-ene (5.14 mL, 34.3 mmol) in 40 mL of ethyl acetate under argon was added a solution of oxazoline C (3.72 g, 8.18 mmol) in 40 mL of trichloromethane. This mixture was stirred at room temperature for 18 hours, at which time cupric bromide (3.83 g, 17.2 mmol) and 1,8-diazabicyclo[5.4.-0]undec-7-ene (2.50 mL, 17.2 mmol) were added. The mixture was stirred at room temperature for 7 hours and poured into a solution of 200 mL of ethyl acetate and 200 mL of 1:1 concentrated ammonium hydroxide solution and saturated ammonium chloride solution. The aqueous layer was separated and extracted with ethyl acetate (3×200 mL). The combined ethyl acetate extracts were dried (magnesium sulfate), filtered and concentrated in vacuo. This material was chromatographed on 140 g of Merck silica gel 60 using 3:2 ethyl acetate-hexane as eluant to give 2.52 g (68%) of oxazole D.

TLC: silica gel, ethyl acetate $R_f$ 0.88, cerium sulfate dip.

$^{13}$C Of 5 (CDCl$_3$, 67.5 MHz) δ: 164.2, 160.3, 140.6, 140.4, 136.5, 136.2, 128.3, 127.9, 127.6, 66.9, 60.2, 54.9, 54.4, 46.8, 46.4, 39.0, 37.4, 37.0, 33.3, 29.8, 26.6, 26.3, 24.1.

E. N-(4-Cyclohexylbutyl)-2-(2-pyrrolidinyl)-4-oxazolecarboxamide

To a stirred mixture of oxazole D (280 mg, 0.62 mmol) in 15 mL of methanol under argon was added 10% palladium on carbon (56 mg, 20% based on the weight of oxazole C). The atmosphere was replaced with hydrogen by several vacuum-fill cycles. The mixture was stirred at room temperature for 22 hours, and the catalyst was filtered off through a 4 μm polycarbonate film. The catalyst was rinsed with methanol (4×15 mL). The filtrate was concentrated in vacuo to give 200 mg of pyrrolidine E in a quantitative yield.

TLC: silica gel, 10% methanol/dichloromethane $R_f$ 0.20, cerium sulfate dip.

F.
2-[[2-[4-[[(4-Cyclohexylbutyl)amino]carbonyl]-2-oxazolyl]-1-pyrrolidinyl]methyl]benzenepropanoic acid, methyl ester To a stirred solution of pyrrolidine E (200 mg, 0.63 mmol) and 3-(2-bromophenyl)propanoic acid, methyl ester (171 mg, 0.63 mmol) in 10 mL of dry tetrahydrofuran under argon was added triethylamine. The mixture was stirred at room temperature for 16 hours and concentrated in vacuo. The crude product was diluted with 150 mL of ethyl acetate and washed with saturated sodium bicarbonate solution (2×30 mL). The ethyl acetate layer was dried (magnesium sulfate), filtered and concentrated in vacuo. Purification was effected by flash chromatography on 25 g of Merck silica gel 60 using 2% methanol/dichloromethane as eluant to give 200 mg (62%) of ester E.

TLC: silica gel, 4% methanol/dichloromethane $R_f$ 0.38, cerium sulfate dip.

$^{13}$C of 8 (CDCl$_3$, 67.5 MHz) δ: 173.6, 164.9, 140.8, 139.9, 136.3, 130.2, 129.2, 126.0, 61.5, 56.8, 53.3, 51.4, 39.1, 37.5, 37.1, 35.4, 33.3, 33.3, 30.4, 29.9, 27.5, 26.6, 26.3, 26.3, 24.2, 22.8.

G.

2-[[2-[4-[[(4-Cyclohexylbutyl)amino]carbonyl]-2-oxazolyl]-1-pyrrolidinyl]methyl]benzenepropanoic acid To a stirred mixture of ester F (190 mg, 0.37 mmol) in 7.5 mL of freshly distilled tetrahydrofuran and 1.86 mL of water under argon was added lithium hydroxide monohydrate (46.8 mg, 1.12 mmol). The mixture was stirred at room temperature for 5 hours, at which time lithium hydroxide monohydrate (43 mg, 1.03 mmol) was added. The mixture was stirred at room temperature for another 17 hours and acidified to pH 2 by the addition of 1N hydrochloric acid solution. The mixture was saturated with sodium chloride and extracted with trichloromethane (4×20 mL). The combined trichloromethane extracts were dried (magnesium sulfate), filtered and concentrated in vacuo. The crude acid was recrystallized in 10 mL of trichloromethane and 30 mL of hexane at room temperature to give 168 mg (87%) of Example 1.

Melting point 155°-156° C.

TLC: silica gel, 10% methanol/dichloromethane $R_f$ 0.22, iodine.

$^{13}$C of 9 (CDCl$_3$, 67.5 MHz) δ: 176.4, 164.8, 160.8, 141.5, 139.9, 135.9, 130.3, 129.2, 127.9, 126.1, 61.6, 56.9, 53.5, 39.3, 37.5, 37.1, 35.5, 33.3, 33.3, 30.3, 29.8, 27.3, 26.7, 26.4, 26.4, 24.2, 22.8.

EXAMPLE 2

(S)-2-[[2-[4-[[(4-Cyclohexylbutyl)amino]carbonyl]-2-oxazolyl]-1-pyrrolidinyl]methyl]benzenepropanoic acid, monolithium salt

A.

(S)-2-[[2-[4-[[(4-Cyclohexylbutyl)amino]carbonyl]-2-oxazolyl]-1-pyrrolidinyl]methyl]benzenepropanoic acid, methyl ester Steps A through E of Example 1 were repeated, starting with N-benzyloxycarbonyl-L-proline to yield the S-isomer of amine D from Example 1. To this compound (88.6 mg, 0.28 mmol) and 3-(2-formylphenyl)-propanoic acid, methyl ester (85.3 mg, 0.44 mmol) in 1 mL of methanol under argon was added sodium cyanoborohydride (34.9 mg, 0.56 mmol) and acetic acid (0.20 mL, 20% based on the volume of methanol). The mixture was stirred at room temperature for 22 hours and then diluted with 5 mL of methanol. The mixture was acidified to pH 1 by the addition of 1N hydrochloric acid solution and stirred at room temperature for 30 minutes. The mixture was concentrated in vacuo. The residue was diluted with 5 mL of water and neutralized with solid sodium bicarbonate. The mixture was extracted with ethyl acetate (4×10 mL). The ethyl acetate extracts were dried (magnesium sulfate), filtered and concentrated in vacuo. Purification was effected by flash chromatography on 16 g of Merck silica gel 60 using 200 mL of each of 1:1 and 1:2 hexane-ether as eluants to give 120 mg (87%) of ester A.

TLC: silica gel, 4% methanol/dichloromethane $R_f$ 0.38, cerium sulfate dip.

B.

(S)-2-[[2-[4-[[(4-Cyclohexylbutyl)amino]carbonyl]-2-oxazolyl]-1-pyrrolidinyl]methyl]benzenepropanoic acid, monolithium salt The S-isomer of Example 1 was prepared from compound A immediately above following the procedures of step G from Example 1. The latter compound (68.5 mg, 0.13 mmol) was combined with 4 mL of 1N lithium hydroxide solution. The mixture was then concentrated in vacuo. This concentrate was dissolved in 3 mL of water and 3 mL of acetonitrile and chromatographed on 14 g of HP-20 gel using 80 mL of water as eluant, followed by elution with 4:1 water-acetonitrile to give 58.1 mg (89%) of Example 2 as a solid.

Melting point 92°-94° C., $[a]_D = -19.7°$, (C=5.64, 50% methanol in water)

TLC: silica gel, 10% methanol/dichloromethane $R_f$ 0.22, iodine.

$^{13}$C NMR of 10 (67.5 MHz, D$_2$O) δ: 182.7, 165.7, 162.5, 143.0, 141.9, 135.9, 135.6, 131.2, 129.8, 128.5, 126.2, 61.8, 56.2, 54.5, 40.0, 39.5, 38.5, 38.1. 34.2, 30.5, 29.5, 27.7, 27.3, 25.1. 23.1.

EXAMPLE 3

(R)-2-[[2-[4-[[(4-Cyclohexylbutyl)amino]carbonyl]-2-oxazolyl]-1-pyrrolidinyl]methyl]benzenepropanoic acid, monolithium salt The procedures of Example 2 were repeated, starting with N-benzyloxycarbonyl-D-proline.

EXAMPLE 4

2-[[5-[4-[[(4-Cyclohexylbutyl)amino]carbonyl]-2-oxazolyl]-1H-imidazol-1-yl]methyl]benzenepropanoic acid A. 1,2-Dihydro-3-methoxynaphthalene See J. B. Press and H. Shechter, *J. Org. Chem.*, 40 (1975), 2446.

A solution of 54.4 g of β-tetralone (0.372 mol) in 800 mL of dimethylformamide (new bottle from Burdick & Jackson, 0.006% water) was cooled to 0° under argon with stirring. A solution of 52.4 g of potassium t-butoxide (0.467 mol, 1.25 equiv) in 200 mL dimethylformamide prepared under argon was rapidly poured into the solution of β-tetralone. A pale reddish color was instantly generated (no precipitate). (Exposure of an aliquot to air gave a dark blue color.) After 60 minutes, 56 g of dimethyl sulfate (0.44 mol, 1.19 equiv) was added quickly by syringe. TLC after 15 minutes indicated nearly complete conversion to product. After the mixture was allowed to warm to room temperature over 90 minutes, TLC was unchanged. The mixture was poured into about 1.5 L of 0.33M aqueous sodium bicarbonate solution. This material was then extracted with hexane (0.5 L, three times). After the extracts were dried over sodium sulfate, the residue was coevaporated with dichloromethane, but not exposed to high vacuum. This procedure produced 62.2 g of crude enol ether A (containing dichloromethane, dimethylformamide, and starting material-related impurities) as an oil. This material was used in the next step without purification.

TLC (15% ethyl acetate in hexanes - anisaldehyde):
β-tetralone 0.38
A 0.72

B. 2-Formylbenzenepropanoic acid, methyl ester

Into 1.0 L of dichloromethane was dissolved 62.2 g of crude enol ether A (containing dichloromethane, dimethylformamide, and β-tetralone-related impurities). After cooling to −78° with stirring, the solution was ozonized using a sparge tube. Ozonation (110 V, 4 SLPM, 5 psi) was carried out until TLC showed disappearance of starting material (about 2 hours); no blue color appeared to this point. The mixture was sparged with oxygen and then warmed to 0° C. To this mixture was added 54.5 g of triphenylphosphine in small portions. TLC showed nearly complete conversion to triphenylphosphine oxide 20 minutes after the last addition. The mixture was warmed to room temperature and stirred overnight. TLC still indicated a trace of triphenylphosphine. After addition of 5.5 g of additional triphenylphosphine, the mixture was concentrated to about 200 mL and stirred at 35° C. for 40 minutes. TLC indicated that triphenylphosphine remained. The remaining solvent was evaporated, and the mixture was diluted with 1 L of hexane and refrigerated for 4 days. Precipitate (largely triphenylphosphine oxide) was filtered, rinsing with hexane. The filtrate was retained. TLC indicated the presence of some desired product in the precipitate. The precipitate was dissolved in a small volume of dichloromethane, and hexane was added to cause reprecipitation. The precipitate was filtered as above. Although TLC indicated a trace of desired product in this second generation precipitate, $^1$H-NMR showed that the quantity was insignificant. The two batches of filtrate were combined and evaporated. Flash chromatography (silica gel, 10% to 15% ethyl acetate in hexane gradient) gave 36.2 g of nearly pure aldehyde B (95% pure=34.4 g) as an oil in 48% overall yield from β-tetralone and 8.7 g of impure material (50% pure=4.3 g, 6% yield)

TLC (15% ethyl acetate in hexanes - anisaldehyde):
A 0.62
B 0.37

$^{13}$C NMR (67.8 MHz in CDCl$_3$): 192.6, 172.9, 142.7, 133.7, 133.4, 131.0, 126.9, 51.5, 35.2, 27.9.

C. 2-(Hydroxymethyl)benzenepropanoic acid, methyl ester

See B. T. Khai and A. Arcelli, Tet. Lett. 26 (1985), 3365.

Into 25 mL of freshly distilled tetrahydrofuran was dissolved 5.15 g of triethylamine (50.1 mmol) under argon. The solution was stirred at room temperature (room temperature bath) as 3.4 g of formic acid (74 mmol) was added dropwise. Vigorous reaction was observed for roughly the first two thirds of the addition. A stream of argon was passed slowly through the reaction vessel. Tris(triphenylphosphine)ruthenium dichloride (0.20 g, 0.21 mmol), was added. The catalyst dissolved to produce a bubbling tan solution. After 2 minutes 10.00 g of nearly pure aldehyde B (95% pure=9.50 g, 49.5 mmol) was added. After 30 minutes, with TLC still indicating the presence of some aldehyde B, triethylamine (1.35 g, 13.4 mmol) and formic acid (1.0 g, 22 mmol) were added. After about 30 minutes more, 1.0 g of formic acid was added. Although TLC still seemed to show a trace of starting material, the mixture was evaporated and then coevaporated with dichloromethane. Flash chromatography (silica gel, 10% to 50% ethyl acetate in hexane gradient) gave 9.05 g of pure alcohol C as an oil. The yield of alcohol C was 94%. Putative residual starting material was also isolated. As judged by $^1$H NMR, this material contained an insignificant trace of starting material. It was largely an unidentified impurity that was present in the starting material.

TLC (25% ethyl acetate in hexanes - anisaldehyde):
B 0.40
C 0.17

$^{13}$C NMR (67.8 MHz in CDCl$_3$): 173.6, 138.4, 128.7, 128.6, 127.9, 126.4, 62.6, 51.5, 35.0, 26.8.

D. 2-[[(Methylsulfonyl)oxy]methyl]benzenepropanoic acid, methyl ester

Into 40 mL of dry dichloromethane was dissolved 6.00 g of alcohol C (30.9 mmol) under argon. The solution was stirred at 0° C. as 6.4 mL of triethylamine (4.7 g, 46 mmol, 1.5 equiv) was added. Then 2.64 mL of mesyl chloride (3.90 g, 34.0 mmol, 1.10 equiv) was added dropwise. Reaction was immediate, and the internal temperature may have exceeded 0° C. A precipitate formed. After 15 minutes, TLC indicated that the starting material was consumed but that two products formed. The mixture was diluted with 80 mL of ice cold hexane. The mixture was then washed with 60 mL of ice-cold 1M aqueous hydrochloric acid twice. The organic layer was dried over sodium sulfate, and the solvent was evaporated. According to $^1$H NMR and MS, the crude product consisted of a 16:10:1 (molar) mixture of mesylate D, the analogous chloride, and alcohol C. This material was used without purification.

TLC (2.5% acetone in toluene - anisaldehyde):
C 0.10
chloride 0.55
D 0.17

E. 2-[[5-[[2-(Trimethylsilyl)ethoxy]carbonyl]-1H-imidazol-1-yl]methyl]benzenepropanoic acid, methyl ester See H. R. Matthews and H. Rapoport, J. Am. Chem. Soc., 95 (1973), 2297 for information pertaining to assignment of structures related to compound E.

To a slurry of 4.33 g of 4-carboxyimidazole 2-trimethylsilylethyl ester (20.4 mmol) in 45 g of dimethylsulfoxide-d$_6$ stirring under argon at room temperature, was added in small portions 0.82 g of 60% sodium hydride dispersion in mineral oil (0.49 g sodium hydride, 20.5 mmol). The mixture foamed, but the reaction was not very exothermic. After 1 hour, foaming had stopped and the mixture was homogeneous. All of the crude mesylate D prepared above (18 mmol, 0.90 equiv of mesylate D assuming 59 mol % purity and 100% mass balance in preparation of mesylate D) was added as a solution in 7 mL of dimethylsulfoxide-d$_6$ with two additional 7 mL portions of solvent to transfer residual mesylate D. The mixture exothermed mildly, and a precipitate formed. TLC indicated nearly complete reaction after 15 minutes, with two major products forming. After stirring overnight the mixture was distilled (60° C., 2 torr) until about 24 g of residue remained. TLC indicated no mesylate D, some chloride, and a trace of 4-carboxyimidazole-2-trimethylsilylethyl ester present. Flash chromatography (silica gel, 15% to 100% ethyl acetate in hexane gradient) allowed isolation of both major products. Nearly pure desired product E, 2.77 g (90% pure=2.50 g, contaminated with 10% of alcohol C) was obtained in 32% yield (based on 4-carboxyimidazole-2-trimethylsilylethyl ester, or 35% based on mesylate D) as an oil. The N-1 alkylated regioisomer of compound E, 4.44 g, was obtained in 56% yield (or 62% based on mesylate D) as an oil. The structures of compound E and its regioisomer were assigned by observation of nOe's in their $^1$H NMR spectra: While compound E showed an nOe between HetCH$_2$C$_6$H$_4$CH$_2$CH$_2$CO$_2$CH$_3$ and only one imidazole ring proton, its N-1 regioisomer showed nOe's to both imidazole ring protons TLC (50% ethyl acetate in hexanes - anisaldehyde):
4-carboxyimidazole 2-trimethylsilylethyl ester 0.06
mesylate D 0.53
E 0.36
E regioisomer 0.15

$^{13}$C NMR (67.8 MHz in CDCl$_3$) of E: 172.9, 160.4, 142.0, 138.1, 137.7, 133.9, 129.2, 128.5, 127.5, 127.1, 123.1, 62.8, 51.7, 47.8, 34.4, 27.1, 17.3, −1.5

$^{13}$C NMR (67.8 MHz in CDCl$_3$) of E regioisomer: 172.7, 162.8, 138.6, 137.9, 134.3, 132.5, 129.4, 129.1, 129.0, 127.1, 124.9, 62.5, 51.6, 48.8, 34.4, 26.7, 17.4, −1.7

F.
2-[(5-Carboxy-1H-imidazol-1-yl)methyl]benzenepropanoic acid, methyl ester This chemistry is described by P. Sieber, R. H. Andreatta, K. Eisler, B. Kamber, B. Riniker, and H. Rink, *Peptides: Proceedings of the Fifth American Peptide Symposium*, (M. Goodman and J. Meienhofer, Eds)., Halsted Press, New York (1977), 543-545.

To a solution of 2.70 g of compound E above (90% pure=2.43 g, 6.28 mmol) in 20 mL of dry dimethylformamide stirring under argon at room temperature, was added 7.0 mL of 1.0M tetrabutylammonium fluoride in tetrahydrofuran solution (7.0 mmol, 1.1 equiv). The mixture bubbled. TLC showed reaction progress after 10 minutes, but after 1 hour little further change had occurred. Additional reagent (7.0 mL) was added. After 1 hour, TLC showed complete reaction. The solvent was coevaporated with toluene. The residue (6.5 g oil) was flash-chromatographed [silica gel, 0% to 10% (25% acetic acid in pyridine) in ethyl acetate gradient] to isolate, after coevaporation with toluene, 1.76 g of pure acid F as a pale yellow solid. The yield of compound F was 97%.

TLC [10% (25% acetic acid in pyridine) in ethyl acetate - anisaldehyde]:
E 0.74
F 0.28

$^{13}$C NMR (67.8 MHz in dimethylsulfoxide-d$_6$): 172.6, 160.9, 143.3, 137.5, 137.0, 135.7, 128.9, 127.4, 126.7, 125.3, 123.0, 51.3, 46.5, 33.7, 26.7.

G.
2-[[5-[[[2-[(4-Cyclohexylbutyl)amino]-1-(hydroxymethyl)-2-oxoethyl]amino]carbonyl]-1H-imidazol-1-yl]methyl]benzenepropanoic acid, methyl ester To a solution of 1.70 g of acid F (5.90 mmol), 1.64 g of amine hydrochloride A (D-isomer) from Example 1 (5.9 mmol, 1.00 equiv) 0.74 g of 1-hydroxybenzotriazole hydrate (5.5 mmol, 0.93 equiv), and 0.87 mL of N-methylmorpholine (0.80 g, 8.0 mmol, 1.35 equiv) in 15 mL of dimethylformamide stirring under argon at room temperature, was added 1.48 g of 1-(3-dimethylaminopropyl)-3-ethylcarbodiimide hydrochloride (7.7 mmol, 1.31 equiv). After about 5 hours, the mixture was coevaporated with toluene. The residue was flash-chromatographed (silica, 5% to 10% methanol in dichloromethane gradient) to provide 3.06 g of a white solid, pure diamide G. The yield of the title compound was quantitative.

TLC ([10%(10% concentrated aqueous ammonia in methanol) in dichloromethane - anisaldehyde]:
F 0.04
N-(4-(cyclohexyl)butyl)-(D)-serinamide hydrochloric acid salt 0.25
G 0.43

$^{13}$C NMR (67.8 MHz in CDCl$_3$): 173.1, 170.4, 160.6, 141.7, 138.2, 134.1, 132.8, 129.3, 128.5, 127.8, 127.1, 125.1, 62.5, 53.8, 51.7, 47.8, 39.6, 37.4, 37.0, 34.4, 33.3, 29.6, 27.2, 26.6, 26.3, 24.0.

H.
2-[[5-[4-[[(4-Cyclohexylbutyl)amino]carbonyl]-4,5-dihydro-2-oxazolyl]-1H-imidazol-1-yl]methyl]benzenepropanoic acid, methyl ester To a solution of 2.97 g of compound G (5.81 mmol) in 24 mL of dry acetonitrile and 6 mL of dichloromethane under argon at room temperature, was added 4.47 g of triphenylphosphine (17.1 mmol, 2.9 equiv), 2.3 g of diisopropylethylamine (17.8 mmol, 3.1 equiv), and finally 2.5 g of carbon tetrachloride (16.4 mmol, 2.8 equiv). After stirring for 3 hours, 1.0M aqueous sodium bicarbonate solution was added, and the mixture was extracted three times with dichloromethane. The combined extracts were dried over sodium sulfate and evaporated to provide 8.7 g of solidifying oil. Flash chromatography (silica, 50% to 100% ethyl acetate in hexane gradient) afforded 2.81 g of a white solid, nearly pure oxazoline H (96% pure=2.70 g). The oxazoline was obtained in 94% yield.

TLC (10% methanol in dichloromethane - anisaldehyde):
G 0.35
H 0.48

$^{13}$C NMR (67.8 MHz in CDCl$_3$): 172.8, 171.2, 158.2, 142.3, 137.2, 136.0, 134.9, 129.2, 128.0, 127.2, 125.7, 120 1, 69.8, 68.8, 51.7, 48.0, 39.1, 37.4, 37.0, 33.9, 33.2, 29.7, 27.2, 26.6, 26.3, 23.9.

I.
2-[[5-[4-[[(4-Cyclohexylbutyl)amino]carbonyl]-2-oxazolyl]-1H-imidazol-1-yl]methyl]benzenepropanoic acid, methyl ester This chemistry is described by D. L. Evans, D. K. Minster, U. Jordis, S. M. Hecht, A. L. Mazzu, Jr., and A. I. Meyers, *J. Org. Chem.*, 44 (1979), 497.

To a solution of 0.35 g of nearly pure oxazoline H (96% pure=0.34 g, 0.71 mmol) in 10 mL of dichloromethane at room temperature, was added 1.08 g of untitrated nickel peroxide, and the heterogenous mixture was stirred at room temperature. The reaction was incomplete after 1 hour. An additional 1.34 g of nickel peroxide was then added. After 6 hours, the reaction mixture was filtered through Celite ® and evaporated to obtain 0.23 g of nearly pure oxazole I (94% pure=0.22 g), a semisolid. The oxazole was obtained in 62% yield. TLC [5% (20 pyridine:6 acetic acid:11 water) in ethyl acetate - anisaldehyde]:
H 0.50
I 0.53

$^{13}$C NMR (67.8 MHz in CDCl$_3$): 172.8, 160.1, 153.9, 140.9, 139.8, 138.0, 137.0, 133.5, 133.5, 129.2, 128.7, 128.0, 127.3, 120.4, 51.7, 48.0, 39.1, 37.5, 37.1, 34.5, 33.3, 29.9, 27.2, 26.6, 26.3, 24.1.

J.
2-[[5-[4-[[(4-Cyclohexylbutyl)amino]carbonyl]-2-oxazolyl]-1H-imidazol-1-yl]methyl]benzenepropanoic acid To a solution of 0.23 g of nearly pure oxazole I (94% pure=0.22 g, 0.45 mmol) in 6 mL of methanol and 4 mL of tetrahydrofuran stirring at room temperature under argon, was added 3 mL of 1.0M aqueous sodium hydroxide solution. After 2 hours, 1.0M aqueous hydrochloric acid solution was added to lower the pH to 6. After addition of brine, the mixture was extracted with dichloromethane (5 times). The extracts were dried over sodium sulfate, and solvent evaporation gave crude Example 4. Flash chromatography [50% to 75% (5% acetic acid in ethyl acetate) in hexane gradient] afforded, after azeotropic removal of acetic acid with toluene, 0.17 g (80% yield) of pure Example 4 as a solid. Melting point 148°14 154°.

TLC [50% (5% acetic acid in ethyl acetate) in hexane - anisaldehyde]:
I 0.17
Example 4 0.05

EXAMPLE 5

2-[[2-[4-[[(4-Cyclohexylbutyl)amino)carbonyl]-2oxazolyl]-5-oxo-1-pyrrolidinyl]methyl]benzenepropanoic acid A. D,L-pyroglutamic acid, t-butyl ester To a stirred mixture of D,L-pyroglutamic acid (2.00 g, 15.5 mmol) in 60 mL of dimethylformamide was added t-butanol (40 mL, 0.42 mol), 1-(3-dimethylaminopropyl)-ethyl carbodiimide hydrochloride salt (2.97 g, 15.5 mmol) and 4-dimethylaminopyridine (3.79 g, 31.0 mmol). This solution was stirred at room temperature for 23 hours and concentrated under pump vacuum at 60° C. The residue was diluted with 200 mL of ethyl acetate and washed with 1N hydrochloric acid solution (3×50 mL), saturated sodium bicarbonate solution (2×50 mL) and brine (1×50 mL). The organic layer was dried (magnesium sulfate), filtered and concentrated in vacuo. This material was chromatographed on 40 g of Merck silica gel 60 using 4% methanol/dichloromethane as eluant to give t-butyl ester A (330 mg,12%).

TLC: silica gel, 4% methanol/dichloromethane $R_f$ 0.37, iodine.

B 2-[[2-[(1,1-Dimethylethoxy)carbonyl]-5-oxo-1-pyrrolidinyl]methyl]benzenepropanoic acid, methyl ester To a stirred suspension of 60% sodium hydride in mineral oil (78.4 mg, 1.96 mmol) in 5 mL of dry tetrahydrofuran under argon at −78° C. was added a solution of t-Butyl ester A (330 mg, 1.78 mmol) in 5 mL of dry tetrahydrofuran. The mixture was stirred at −78° C. for 30 minutes, at which time a solution of 3-(2-bromomethylphenyl)propanoic acid, methyl ester in 5 mL of dry tetrahydrofuran was added. The reaction mixture was then stirred at room temperature for 6 hours, and 15 mL of dry tetrahydrofuran was added. The mixture was stirred at room temperature for another 18 hours and quenched with acetic acid (2 mL). The mixture was concentrated in vacuo. The crude product was diluted with 200 mL of ethyl acetate and washed with saturated sodium bicarbonate solution (2×50 mL) and brine (1×50 mL). The ethyl acetate layer was dried (magnesium sulfate), filtered and concentrated in vacuo. This material was chromatographed on 25 g of Merck silica gel 60 using 1:4 hexane-ether as eluant to give 320 mg (48%) of amide B.

TLC: silica gel, 4% methanol/dichloromethane $R_f$ 0.62, cerium sulfate.

C.
2-[(2-Carboxy-5-oxo-1-pyrrolidinyl)methyl]benzenepropanoic acid, methyl ester To amide B (300 mg, 0.83 mmol) at 0° C. was added a 0° C. 4N hydrochloric acid solution in dioxane (10 mL). The mixture was stirred at 0° C. for 1 hour and at room temperature for 4 hours. The mixture was concentrated in vacuo and diluted with 10 mL of benzene and concentrated in vacuo. This material was chromatographed on 20 g of Merck silica gel 60 using 4% methanol/dichloromethane as eluant to give 170 mg (67%) of acid C.

TLC: silica gel, 0.6% acetic acid in 4% methanol/dichloromethane $R_f$ 0.34, cerium sulfate D.
2-[[[2-[[[2-[(4-Cyclohexylbutyl)amino]-1-(hydroxymethyl)-2-oxoethyl]amino]carbonyl]-5-oxo-1-pyrrolidinyl]methyl]benzenepropanoic acid, methyl ester; and E.
(E)-3-[2-[[[2-[[[2-[(4-Cyclohexylbutyl)amino]-1-(hydroxymethyl)-2-oxoethyl]amino]carbonyl]-5-oxo-1-pyrrolidinyl]methyl]phenyl]propenoic acid, methyl ester To a stirred mixture of acid C (165 mg, 0.54 mmol), 1-hydroxybenzotriazole monohydrate (91 mg, 0.54 mmol) and amine hydrochloride A from Example 1 (151 mg, 0.54 mmol) and triethylamine (0.22 mL, 1.62 mmol) in 5 mL of dimethylformamide was added ethyl-3-(3-dimethylamino)propylcarbodiimide hydrochloride salt (104 mg, 0.54 mmol). The mixture was stirred at room temperature for 19 hours and concentrated in vacuo. The residue was diluted with 150 mL of ethyl acetate and washed with 1N hydrochloric acid solution (3×30 mL), 0.2N sodium hydroxide solution (2×30 mL), saturated sodium bicarbonate solution (1×30 mL) and brine (1×60 mL). The ethyl acetate layer was dried (magnesium sulfate), filtered and concentrated in vacuo. This material was chromatographed on 22 g of Merck silica gel 60 using 6% methanol/dichloromethane as eluant to give 150 mg (52%) of amides D and E. (The presence of amide E was due to contamination of methyl ortho-bromomethylcinnamate in the bromo compound used in step B).

TLC: silica gel, 6% methanol/dichloromethane $R_f$, 7, 0.29; 8, 0.32, cerium sulfate.

To a stirred mixture of amides D and E under argon at room temperature in 10 mL of methanol was added 10% palladium on carbon (25 mg, 16% based on the weight of amides D and E). The atmosphere was switched to hydrogen with several vacuum-fill cycles. The reaction mixture was stirred at room temperature for 4 hours. The catalyst was filtered off through a 4 μM polycarbonate film and rinsed with methanol (3×15 mL). The filtrate was concentrated in vacuo to give 160 mg (100%) of pure amide D.

TLC: silica gel, 6% methanol/dichloromethane $R_f$ 0.29, cerium sulfate.

F.
2-[[2-[4-[[(4-Cyclohexylbutyl)amino]carbonyl]-4,5-dihydro-2-oxazolyl]-5-oxo-1-pyrrolidinyl]methyl]benzenepropanoic acid, methyl ester To a stirred mixture of pure amide D (160 mg, 0.30 mmol) and triethylamine (0.08 mL, 0.60 mmol) under argon at 0° C. was added mesyl chloride (0.029 mL, 0.38 mmol). The mixture was stirred at 0° C. for 1 hour and concentrated in vacuo. The residue was diluted with 20 mL of acetone and combined with potassium carbonate (0.41 g, 3.00 mmol). The reaction mixture was refluxed under argon for 4.5 hours and cooled to room temperature. The solid was filtered off and rinsed with acetone (4×30 mL). The filtrate was concentrated in vacuo and chromatographed on 24 g of Merck silica gel 60 using 4% methanol/dichloromethane as eluant to give 152 mg (98%) of oxazoline F.

TLC: silica gel, 6% methanol/dichloromethane $R_f$ 0.68, cerium sulfate.

G.
2-[[2-[4-[[(4-Cyclohexylbutyl)amino]carbonyl]-2-oxazolyl]-5-oxo-1-pyrrolidinyl]methyl]benzenepropanoic acid, methyl ester To a stirred mixture of cupric bromide (138 mg, 0.62 mmol) under argon at room temperature in 1 mL of ethyl acetate was added 1,8-diazabicyclo[5.4.0]undec-7-ene (0.18 mL, 1.23 mmol). The mixture was stirred at room temperature for 30 minutes, at which time a solution of oxazoline G (150 mg, 0.29 mmol) in 1 mL of chloroform was added. The mixture was stirred at room temperature for 20 hours and then cupric bromide (69 mg, 0.31 mmol) and 1,8-diazabicyclo[5.4.0]undec-7-ene (0.045 mL, 0.31 mmol) were added. The mixture was stirred at room temperature for 8 hours and another batch of cupric bromide (69 mg, 0.31 mmol) and 1,8-diazabicyclo[5.4.0]undec-7-ene (0.09 mL, 0.62 mmol) were added. The reaction mixture was stirred for another 18 hours and again cupric bromide (69 mg, 0.31 mmol) and 1,8-diazabicyclo[5.4.0]undec-7-ene (0.045 mL, 0.31 mmol) were added. The mixture was stirred at room temperature for 6.5 hours and cupric bromide (69 mg, 0.31 mmol) and 1,8-diazabicyclo[5.4.0]undec-7-ene (0.045 mL, 0.31 mmol) were added. The reaction mixture was stirred at room temperature for 16 hours and poured into a mixture of 40 mL of ethyl acetate and 40 mL of 1:1 saturated ammonium chloride solution and concentrated ammonium hydroxide solution. The aqueous layer was separated and extracted with ethyl acetate (3×40 mL). The combined ethyl acetate extracts were dried (magnesium sulfate), filtered and concentrated in vacuo. Purification was effected by flash chromatography on 25 g of Merck silica gel 60 using 2% methanol/dichloromethane as eluant to give 111 mg (41%) of oxazole G.

TLC: silica gel, 2% methanol/dichloromethane $R_f$ 0.24, cerium sulfate.

H.
2-[2-[4-[[(4-Cyclohexylbutyl)amino]carbonyl]-2-oxazolyl]-5-oxo-1-pyrrolidinyl]methyl]benzenepropanoic acid To a stirred mixture of oxazole H (58 mg, 0.11 mmol) under argon in 2 mL of freshly distilled tetrahydrofuran and 0.5 mL of water was added lithium hydroxide monohydrate (14.3 mg, 0.34 mmol). The mixture was stirred at room temperature for 15 hours and acidified to pH 2 by the addition of 1N hydrochloric acid solution. The resulting mixture was diluted with 5 mL of water and extracted with ethyl acetate (4×30 mL). The combined ethyl acetate extracts were dried (magnesium sulfate), filtered and concentrated in vacuo. Purification was effected by flash chromatography on 15 g of Merck silica gel 60 using 0.3% acetic acid in 4% methanol/dichloromethane as eluant to give 45 mg (80%).

Melting point 151°-153° C.

TLC: silica gel, 0.3% acetic acid in 4% methanol/dichloromethane $R_f$ 0.34, iodine.

$^{13}C$ NMR of 12 (67.5 MHz, CDCl$_3$)δ: 176.0, 175.0, 162.3, 160.1, 141.7, 139.3, 136.4, 132.8, 129.7, 129.3, 128.4, 126.6, 54.5, 42.9, 39.2, 37.5, 37.0, 35.0, 33.3, 29.8, 29.5, 27.0, 26.6, 26.3, 24.2, 23.9.

EXAMPLE 6
(S)-2-[[2-Oxo-5-[4-[[(2-phenylethyl)amino]carbonyl]-2-oxazolyl]-1-pyrrolidinyl]methyl]benzenepropanoic acid

A.
N-[2-(4-Chlorophenyl)ethyl]-N$^2$-[(1,1-dimethylethoxy)carbonyl]-L-serinamide To a stirred mixture of N-butoxycarbonyl-L-serine (20 g, 97.6 mmol), 1-Hydroxybenzotriazole (16.5 g, 97.6 mmol), 2-(4-chlorophenyl)ethylamine (15.2 g, 97.6 mmol) and triethylamine (27.2 mL, 195 mmol) in 250 mL of dimethylformamide under argon at 0° C. was added ethyl-3-(3-dimethylamino)propylcarbodiimide hydrochloride salt (18.7 g, 97.6 mmol). The mixture was stirred at room temperature for 18 hours and concentrated in vacuo. The residue was diluted with 700 mL of ethyl acetate and washed with 0.2N sodium hydroxide solution (2×200 mL), 1N hydrochloric acid solution (3×300 mL), saturated sodium bicarbonate solution (1×300 mL) and brine (1×100 mL). The organic layer was dried (magnesium sulfate), filtered and concentrated in vacuo. The crude product was recrystallized in ethyl acetate-hexane to give 28 g (84%) of amide A.

TLC: silica gel, 2% methanol/dichloromethane $R_f$ 0.20, cerium sulfate.

B.
N-[2-(4-Chlorophenyl)ethyl]-N$^2$-[(1,1-dimethylethoxy)carbonyl]-L-serinamide To a stirred mixture of amide A (24.8 g, 72.4 mmol) in 350 mL of dichloromethane and 50 mL of chloroform at 0° C. was added trifluoroacetic acid (50 mL, 649 mmol). The mixture was stirred at room temperature for 3 hours and then more trifluoroacetic acid (20 mL, 260 mmol) was added. The reaction mixture was stirred at room temperature for another 2.5 hours. The mixture was diluted with 400 mL of toluene and concentrated in vacuo. The residue was combined with 500 mL of ether and methanol was added until the mixture became homogeneous. To this mixture was added 30 mL of 4N hydrochloric acid in ether. The mixture was concentrated in vacuo and triturated in ether to give 19.6 g (97%) of amine hydrochloride B.

C.
(S)-N-[2-(4-Chlorophenyl)ethyl]-N$^2$-[5-(1,1-dimethylethoxy)-1,5-dioxo-2-[[(phenylmethoxy)carbonyl]amino]pentyl]-L-serinamide To a stirred mixture of carbobenzoxy-L-glutamic acid-t-butyl ester (3.00 g, 8.90 mmol), amine hydrochloride B (2.48 g, 8.90 mmol), 1-hydroxybenzotriazole monohydrate (1.50 g, 8.90 mmol) and 4-methylmorpholine (2.15 mL, 19.6 mmol) in 60 mL of dimethylformamide under argon was added ethyl-3-(3-dimethylamino)propylcarbodiimide hydrochloride salt (1.71 g, 8.90 mmol). The reaction mixture was stirred at room temperature for 44 hours and concentrated in vacuo. The residue was diluted with 400 mL of ethyl acetate and washed with 1N lithium hydroxide solution (3×100 mL), 1N hydrochloric acid solution (3×100 mL), saturated sodium bicarbonate solution (1×100 mL) and brine (1×100 mL). The organic layer was dried (magnesium sulfate), filtered and concentrated in vacuo to give 4 g (80%) of alcohol C.

TLC: silica gel, 4% methanol/dichloromethane $R_f$ 0.34, cerium sulfate.

D. (S)-N-[2-(4-Chlorophenyl)ethyl]-2-[4-[(1,1-dimethylethoxy)carbonyl]-4-oxo-1-[[(phenylmethoxy)carbonyl]amino]butyl]-4,5-dihydro-4-oxazolecarboxamide To a stirred mixture of alcohol C (4.00 g, 7.12 mmol) and triphenylphosphine (3.73 g, 14.2 mmol) in 5.5 mL of dichloromethane, 22 mL of chloroform and 27.5 mL of acetonitrile under argon in a cold water bath was added sequentially diisopropylethylamine (2.48 mL, 14.2 mmol) and carbon tetrachloride (1.37 mL, 14.2 mmol). The mixture was stirred under argon in a cold water bath for 2 hours and at room temperature for 2.5 hours. The mixture was diluted with 200 mL of ethyl acetate at 0° C. and then combined slowly with 100 mL of saturated sodium bicarbonate solution. The aqueous layer was separated and extracted with ethyl acetate (1×200 mL). The combined ethyl acetate extracts were dried (magnesium sulfate), filtered and concentrated in vacuo. This material was chromatographed on 220 g of Merck silica gel 60 using 20% acetone in toluene as eluant to give 2.72 g (70%) of oxazoline D.

TLC: silica gel, 20% acetone in toluene $R_f$ 0.34, cerium sulfate.

E. (S)-N-[2-(4-Chlorophenyl)ethyl]-2-[4-[(1,1-dimethylethoxy)carbonyl]-4-oxo-1-[[(phenylmethoxy)carbonyl]amino]butyl]-4-oxazolecarboxamide To a stirred mixture of cupric bromide (2.27 g, 10.2 mmol) in 15 mL of ethyl acetate under argon at room temperature was added 1,8-diazabicyclo-[5.4.0]undec-7-ene (3.04 mL, 20.3 mmol). The mixture was stirred at room temperature for 30 minutes, at which time a solution of oxazoline D (2.63 g, 4.84 mmol) in 15 mL of chloroform was added. The mixture was stirred at room temperature for 17 hours and another batch of cupric bromide (2.27 g, 10.2 mmol) and 1,8-diazabicyclo[5.4.0]undec-7-ene (1.52 mL, 10.2 mmol) was added. The mixture was stirred at room temperature for 6 hours and cupric bromide (2.27 g, 10.2 mmol) and 1,8-diazabicyclo[5.4.0]undec-7-ene (1.52 mL, 10.2 mmol) were added. The mixture was stirred at room temperature for 19 hours, at which time again cupric bromide (2.27 g, 10.2 mmol) and 1,8-diazabicyclo[5.4.0]undec-7-ene (1.52 mL, 10.2 mmol) were added. The mixture was stirred at room temperature for 6 hours and a last batch of cupric bromide (2.27 g, 10.2 mmol) and 1,8-diazabicyclo[5.4.0]undec-7-ene (1.52 mL, 10.2 mmol) was added. The reaction mixture was stirred at room temperature for 17 hours and then poured into a mixture of 400 mL of ethyl acetate and 360 mL of a solution of 1:1 concentrated ammonium hydroxide solution and saturated ammonium chloride solution. The aqueous layer was separated and extracted with ethyl acetate (2×400 mL). The combined ethyl acetate extracts were dried (magnesium sulfate), filtered and concentrated in vacuo. Purification was effected by flash chromatography on 240 g of Merck silica gel 60 using 15% acetone in toluene as eluant to give 0.77 g (29%) of oxazole E and 0.43 g (16%) of recovered oxazoline D.

TLC: silica gel, 20% acetone in toluene $R_f$ 0.41, cerium sulfate.

F. (S)-2-[1-Amino-4-[(1,1-dimethylethoxy)carbonyl]-4-oxobutyl]-N-(2-phenylethyl)-4-oxazolecarboxamide To a stirred mixture of oxazole E (750 mg, 1.39 mmol) in 20 mL of methanol under argon was added 20% palladium hydroxide on carbon (106 mg, 14% based on the weight of 8). The atmosphere was switched to hydrogen with several vacuum-fill cycles. The mixture was stirred at room temperature for 7 hours and the catalyst was filtered off through a 4 μM polycarbonate film. The solid was rinsed with methanol (4×15 mL). The filtrate was concentrated in vacuo and chromatographed on 40 g of Merck silica gel 60 using 2% methanol/dichloromethane as eluant to give 460 mg (81%) of amine F.

TLC: silica gel, 4% methanol/dichloromethane $R_f$ 0.47, iodine.

G. (S)-2-[[[4-[(1,1-Dimethylethoxy)carbonyl]-4-oxo-1-[4-[[(2-phenylethyl)amino]carbonyl]-2-oxazolyl]butyl]amino]methyl]benzenepropanoic acid, methyl ester To a stirred mixture of amine F (398 mg, 0.98 mmol) and the aldehyde used in step A of Example 2 (187 mg, 0.98 mmol) in 10 mL of absolute ethanol under argon at room temperature was added 400 mg of powdered dry molecular sieve 4A. The mixture was stirred at room temperature for 6 hours at which time sodium cyanoborohydride (73.6 mg, 1.17 mmol) was added. To this mixture was then added acetic acid (2 mL, 20% of the volume of ethanol) and the pH of the mixture was 4. The mixture was stirred at room temperature for 23 hours and acidified to pH 1 by the addition of 1N hydrochloric acid solution. The mixture was stirred at room temperature for 10 minutes and then diluted with 35 mL of water. The solid was filtered off through a 2-inch pad of Celite® and rinsed with ethyl acetate (6×30 mL). The filtrate was saturated with sodium chloride and the organic layer was separated. The aqueous layer was extracted with ethyl acetate (3×60 mL). The organic extracts were dried (magnesium sulfate), filtered and concentrated in vacuo. This material was chromatographed on 45 g of Merck silica gel 60 using 240 mL of each of 1%, 2% and 6% methanol in dichloromethane as eluants to give 233 mg (41%) of t-butyl ester G and 106 mg (28%) of starting amine F.

TLC: silica gel, 4% methanol/dichloromethane $R_f$ 0.54, iodine.

H. (S)-2-[[2-Oxo-5-[4-[[(2-phenylethyl)amino]carbonyl]-2-oxazolyl]-1-pyrrolidinyl]methyl]benzenepropanoic acid, methyl ester To a stirred mixture of t-butyl ester G (200 mg, 0.34 mmol) in 5 mL of dichloromethane at 0° C. under argon was added trifluoroacetic acid (5 mL, equal volume of dichloromethane). The mixture was stirred at 0° C. for 30 minutes and at room temperature for 2 hours. The mixture was diluted with 100 mL of toluene and concentrated in vacuo. The residue was dissolved in 20 mL of chloroform and combined with 200 mg of dry molecular seive 4A. The mixture was stirred at room temperature for 23 hours and the solid was filtered off. The solid was rinsed with ethyl acetate (3×30 mL). The filtrate was concentrated in vacuo. This material was chromatographed on 24 g of Merck silica gel 60 using 2% methanol/dichloromethane as eluant to give 97.5 mg (56%) of lactam H.

TLC: silica gel, 4% methanol/dichloromethane $R_f$ 0.40, iodine.

I.

(S)-2-[[2-Oxo-5-[4-[[(2-phenylethyl)amino]carbonyl]-2-oxazolyl]-1-pyrrolidinyl]methyl]benzenepropanoic acid To a stirred mixture of lactam H (110 mg, 0.22 mmol) in 4 mL of tetrahydrofuran and 1 mL of water under argon at room temperature was added lithium hydroxide monohydrate (27.2 mg, 0.65 mmol). The mixture was stirred at room temperature for 6 hours and acidified to pH 2 by the addition of 1N hydrochloric acid solution. The mixture was diluted with 10 mL of water, saturated with sodium chloride and extracted with ethyl acetate (4×30 mL). The combined ethyl acetate extracts were dried (magnesium sulfate), filtered and concentrated in vacuo. Purification was effected by flash chromatography on 10 g of Merck silica gel 60 using 0.5% acetic acid in 4% methanol/dichloromethane as eluant to give Example 6.

TLC: silica gel, 0.5% acetic acid in 4% methanol/dichloromethane $R_f$ 0.32, iodine.

$^{13}$C NMR of 13 (67.5 MHz, CDCl$_3$) δ: 176.3, 175.0, 162.2, 160.2, 141.9, 139.2, 138.5, 136.1, 132.6, 129.6, 129.2, 128.7, 128.5, 128.3, 126.6, 126.5, 54.3, 42.8, 40.3, 35.5, 34.9, 29.4, 26.9, 23.8.

EXAMPLE 7

2-[[2-[4-[[(4-Cyclohexylbutyl)amino]carbonyl]-2-oxazolyl]-1-pyrrolidinyl]carbonyl]benzenepropanoic acid A. 3-(2-Carboxyl)benzenepropanoic acid, methyl ester To a stirred mixture of 3-(2-hydroxymethyl)phenylpropanoic acid, methyl ester (250 mg, 1.29 mmol) in 10 mL of acetone was added manganese sulfate-treated Jones reagent (about 2 mL) until an orange-red color persisted. The mixture was stirred at room temperature for 2 hours and then quenched with isopropyl alcohol. This mixture was concentrated in vacuo. The crude product was partitioned between 20 mL of 3M sodium bisulfite solution and ethyl acetate (3×60 mL). The combined ethyl acetate extracts were washed once with 60 mL of brine, dried (magnesium sulfate), filtered and concentrated in vacuo to give 270 mg of acid A in a quantitive yield.

TLC silica gel, 10% methanol/dichloromethane $R_f$ 0.35, iodine.

B.

2-[[2-[4-[[(4-Cyclohexylbutyl)amino]carbonyl]-2-oxazolyl]-1-pyrrolidinyl]carbonyl]benzenepropanoic acid, methyl ester To a stirred mixture of acid A (270 mg, 1.29 mmol) in 15 mL of dry methylene chloride under argon at 0° C. was added a 2M solution of oxalyl chloride in methylene chloride (0.78 mL, 1.55 mmol) over 5 minutes. The mixture was stirred at 0° C. for 2 hours, at which time a solution of amine E from Example 1 (290 mg, 0.91 mmol) and triethylamine (0.43 mL, 3.09 mmol) in 15 mL of methylene chloride over 10 minutes. This mixture was stirred at 0° C. for 1 hour and diluted with 200 m of ethyl acetate. The resulting solution was washed with 1N hydrochloric acid solution (3×20 mL), saturated sodium bicarbonate solution (3×20 mL) and brine (1×30 mL). The organic layer was dried (magnesium sulfate), filtered and concentrated in vacuo. This material was chromatographed on 40 g of Merck silica gel 60 using 2% methanol/dichloromethane as eluant to give 154 mg (36%) of amide B.

TLC: silica gel, 4% methanol/dichloromethane $R_f$ 0.42, cerium sulfate.

$^{13}$C NMR of 4 (67.5 MHz, CDCl$_3$) δ: 173.1, 169.7, 163.7, 160.4, 140.7, 137.1, 136.4, 129.6, 129.4, 126.4, 126.0, 56.4, 53.9, 51.5, 49.0, 39.1, 37.4, 37.0, 35.0, 33.3, 31.0, 30.0, 28.1, 26.6, 26.3, 24.5, 24.2.

C.

2-[[2-[4-[[(4-Cyclohexylbutyl)amino]carbonyl]-2-oxazolyl]-1-pyrrolidinyl]carbonyl]benzenepropanoic acid To a stirred mixture of amide B (150 mg, 0.29 mmol) in 6 mL of freshly distilled tetrahydrofuran and 1.5 mL of water was added lithium hydroxide monohydrate (74 mg, 1.77 mmol). The mixture was stirred at room temperature for 3 hours and acidified to pH 3 by the addition of 1N hydrochloric acid solution. The mixture was concentrated in vacuo and diluted with 10 mL of water. The resulting mixture was saturated with sodium chloride and extracted with ethyl acetate (4×20 mL). The combined ethyl acetate extracts were dried (magnesium sulfate), filtered and concentrated in vacuo. This material was chromatographed on 12 g of Merck silica gel 60 using 0.25% acetic acid in 6% methanol/dichloromethane as eluant to give 131 mg (90%) of Example 7 as an oil.

TLC: silica gel, 0.25% acetic acid in 6% methanol/dichloromethane $R_f$ 0.54, cerium sulfate.

EXAMPLE 8

(2S-cis)-2-[[2-[4-[[[2-(4-Chlorophenyl)ethyl]amino]carbonyl-2-oxazolyl]-4-hydroxy-1-pyrrolidinyl]carbonyl]-benzenepropanoic acid

A.

N-benzyloxycarbonyl-3-thexyldimethylsilyloxyproline, methyl ester

To a stirred mixture of N-benzyloxycarbonyl-3-hydroxyproline, methyl ester (5.00 g, 17.9 mmol), 4-dimethylaminopyridine (22 mg, 0.18 mmol) and triethylamine (2.50 mL, 20.6 mmol) in 50 mL of dry dichloromethane was added thexyldimethylsilyl chloride (3.90 mL, 19.7 mmol). The mixture was stirred at room temperature for 24 hours, at which time thexyldimethylsilyl chloride (2.00 mL, 9.90 mmol) and triethylamine (2.00 mL, 15.4 mmol) were added. The mixture was stirred at room temperature for 24 hours and then diluted with 100 mL of ether. The mixture was cooled to −5° C. and the solid was filtered off. The filtrate was concentrated in vacuo. This material was chromatographed on 180 g of Merck silica gel 60 using 2:1 hexane-ether as eluant to give 4.90 g (81%) of ester A.

TLC: silica gel, 2:1 hexane-ether $R_f$ 0.25, iodine.

B.
N-benzyloxycarbonyl-3-thexyldimethylsilyloxyproline

To a stirred mixture of ester A (4.60 g, 7.18 mmol) in 80 mL of freshly distilled tetrahydrofuran and 20 mL of water was added lithium hydroxide monohydrate (0.90 g, 21.5 mmol). The mixture was stirred at room temperature for 26 hours. The mixture was concentrated in vacuo and diluted with 40 mL of water. The mixture was acidified to pH 2 by the addition of 1N hydrochloric acid solution and saturated with sodium chloride. The mixture was extracted with ethyl acetate (4×100 mL). The ethyl acetate extracts were dried (magnesium sulfate), filtered and concentrated in vacuo to give acid B (4.30 g, 96%).

TLC: silica gel, 4% methanol/dichloromethane $R_f$ 0.30, iodine.

C.
(S)-N-[2-(4-Chlorophenyl)ethyl]-$N^2$-[4-[[dimethyl(1,1,2-trimethylpropyl)silyl]oxy]-1-[(phenylmethoxy)carbonyl]-L-prolyl]-L-serinamide To a stirred mixture of acid B (4.20 g, 6.70 mmol), 1-hydroxybenzotriazole hydrate (1.13 g, 6.70 mmol) and N-(2-(2-chlorophenyl)ethyl)-2-aminoacetamide, monohydrochloride (1.87 g, 6.70 mmol) in 60 mL of dimethylformamide under argon was added 4-methylmorpholine (2.21 mL, 20.1 mmol) and ethyl-3-(3-dimethylamino)propylcarbodiimide hydrochloride salt (1.28 g, 6.70 mmol). The mixture was stirred at room temperature for 24 hours and concentrated in vacuo. The residue was diluted with 400 mL of ethyl acetate and washed with 0.2N sodium hydroxide solution (3×100 mL), 1N hydrochloric acid solution (2×100 mL), saturated sodium bicarbonate solution (1×100 mL) and brine (1×100 mL). The organic layer was dried (magnesium sulfate), filtered and concentrated in vacuo. This material was chromatographed on 300 g of Merck silica gel 60 using 2.5% methanol/dichloromethane as eluant to give amide C (3.13 g, 48%).

TLC: silica gel, 2% methanol/dichloromethane $R_f$ 0.15, iodine.

D.
(S)-N-[2-(4-Chlorophenyl)ethyl]-2-[4-[[dimethyl(1,1,2-trimethylpropyl)silyl]oxy]-1-[(phenylmethoxy)carbonyl]-L-prolyl]-4,5-dihydro-4-oxazolecarboxamide To a stirred mixture of amide C (1.50 g, 2.38 mmol) in 20 mL of dry dichloromethane under argon at 0° C. was added in order triethylamine (0.66 mL, 4.75 mmol) and mesyl chloride (0.23 mL, 2.97 mmol). The mixture was stirred at 0° C. for 30 minutes and at room temperature for 1 hour. The mixture was concentrated in vacuo and diluted with 20 mL of acetone. The mixture was combined with anhydrous potassium carbonate (1.64 g, 11.9 mmol). The mixture was refluxed for 4 hours and cooled to room temperature. The solid was filtered off and the filtrate was concentrated in vacuo. Purification was effected by flash chromatography using 2.5% methanol/dichloromethane as eluant to give 630 mg (55%) of oxazoline D.

TLC: silica gel, 2% methanol/dichloromethane $R_f$ 0.25, iodine.

E.
(S)-N-[2-(4-Chlorophenyl)ethyl]-2-[4-[[dimethyl(1,1,2-trimethylpropyl)silyl]oxy]-1-[(phenylmethoxy)carbonyl]-L-prolyl]-4-oxazolecarboxamide To a stirred mixture of cupric bromide (612 mg, 2.74 mmol) in 6 mL of ethyl acetate under argon was added 1,8-diazabicyclo[5.4.0]undec-7-ene (0.82 mL, 5.48 mmol). The mixture was stirred at room temperature for 30 minutes, at which time a solution of oxazoline D (800 mg, 1.30 mmol) in 6 mL of trichloromethane was added. The mixture was stirred at room temperature for 16 hours and another batch of cupric bromide (153 mg, 0.69 mmol) and 1,8-diazabicyclo[5.4.0]undec-7-ene (0.10 mL, 0.67 mmol) was added. The mixture was stirred at room temperature for 8 hours and again cupric bromide (204 mg, 0.91 mmol) and 1,8-diazabicyclo[5.4.0]undec-7-ene (0.27 mL, 1.81 mmol) were added. The mixture was stirred at room temperature for 16 hours, at which time a final batch of cupric bromide (204 mg, 0.91 mmol) and 1,8-diazabicyclo[5.4.0]undec-7-ene (0.27 mL, 1.81 mmol) was added. The mixture was stirred at room temperature for 4 more hours and poured into a mixture of 150 mL of ethyl acetate and 80 mL of a 1:1 mixture of concentrated ammonium hydroxide solution and saturated ammonium chloride solution. The aqueous layer was separated and extracted with ethyl acetate (3×100 mL). The combined ethyl acetate extracts were dried (magnesium sulfate), filtered and concentrated in vacuo. This material was chromatographed on 40 g of Merck silica gel 60 using 3:2 ether-hexane as eluant to give 550 mg (68%) of oxazole E.

TLC: silica gel, 2:1 ether-hexane $R_f$ 0.34, iodine.

F.
(S)-N-[2-(4-Chlorophenyl)ethyl]-2-[4-[[dimethyl(1,1,2-trimethylpropyl)silyl]oxy]-L-prolyl]-4-oxazolecarboxamide, hydrochloride To a stirred mixture of oxazole E (70.5 mg, 0.12 mmol) in 3 mL of dry dichloromethane under argon at −10° C. was added a 1M solution of boron tribromide in dichloromethane (0.60 mL, 0.60 mmol). The mixture was stirred at 0° C. for 1.5 hours and at room temperature for 4 hours. The mixture was quenched at 0° C. under argon with water slowly. The mixture was then diluted with 6 mL of 1N hydrochloric acid solution and extracted with trichloromethane (4×20 mL). The trichloromethane extracts were dried (magnesium sulfate), filtered and concentrated in vacuo to give 43 mg (73%) of amine hydrochloride salt F.

TLC: silica gel, 4% methanol/dichloromethane $R_f$ 0.48, iodine.

G.
(2S-cis)-2-[[2-[4-[[[2-(4-Chlorophenyl)ethyl]amino]carbonyl]-2-oxazolyl]-4-thexyldimethylsilyloxy-1-pyrrolidinyl]carbonyl]benzenepropanoic acid, methyl ester To a stirred mixture of amine hydrochloride salt F (45 mg, 0.09 mmol), 1-hydroxybenzotriazole hydrate (14.7 mg, 0.09 mmol) and 3-(2-carboxyl)benzenepropanoic acid, methyl ester (18.2 mg, 0.09 mmol) in 1 mL of dimethylformamide was added in order 4-methylmorpholine (0.03 mL, 0.26 mmol) and ethyl-3-(3-dimethylamino)propylcarbodiimide hydrchloride salt (16.7 mg, 0.09 mmol). The mixture was stirred at room temperature for 18 hours and then diluted with 40 mL of ethyl acetate. The mixture was washed with 0.2N sodium hydroxide solution (2×15 mL), 1N hydrochloric acid solution (2×15 mL), saturated sodium bicarbonate solution (1×15 mL) and brine (1×15 mL). The organic layer was dried (magnesium sulfate), filtered and concentrated in vacuo. This material was chromatographed on 8 g of Merck silica gel 60 using 2% methanol/dichloromethane as eluant to give 35 mg (60%) of amide G.

TLC: silica gel, 4% methanol/dichloromethane $R_f$ 0.42, iodine.

H.
(2S-cis)-2-[[2-[4-[[[2-(4-Chlorophenyl)ethyl]amino]carbonyl]-2-oxazolyl]-4-hydroxy-1-pyrrolidinyl]carbonyl]-benzenepropanoic acid, methyl ester To a stirred mixture of amide G (220 mg, 0.33 mmol) in 3 mL of dry tetrahydrofuran under argon was added a 1M n-tetrabutylammonium fluoride solution in tetrahydrofuran (1.00 mL, 1.00 mmol). The mixture was stirred at room temperature for 3.5 hours and then poured into a mixture of 20 mL of saturated ammonium chloride solution and 30 mL of ethyl acetate. The aqueous layer was separated and extracted with ethyl acetate (3×30 mL). The combined organic extracts were dried (magnesium sulfate), filtered and concentrated in vacuo. Purification was effected by flash chromatography on 24 g of Merck silica gel 60 using 2% methanol/dichloromethane as eluant to give 131 mg (74%) of ester H.

TLC: silica gel, 4% methanol/dichloromethane $R_f$ 0.46, iodine.

I.
(2S-cis)-2-[[2-[4-[[[2-(4-Chlorophenyl)ethyl]amino]carbonyl]-2-oxazolyl]-4-hydroxy-1-pyrrolidinyl]carbonyl]-benzenepropanoic acid To a stirred mixture of ester H (128 mg, 0.24 mmol) in 4 mL of freshly distilled tetrahydrofuran and 1 mL of water was added lithium hydroxide monohydrate (29.9 mg, 0.71 mmol). The mixture was stirred at room tempereature for 8 hours and acidified to pH 2 by the addition of 1N hydrochloric acid solution. The mixture was diluted with 10 mL of water, saturated with sodium chloride and extracted with ethyl acetate (4×30 mL). The ethyl acetate extracts were dried (magnesium sulfate), filtered and concentrated in vacuo. This material was chromatographed on 10 g of Merck silica gel 60 using 150 mL each of 2% methanol/dichloromethane, 1% acetic acid in 4% methanol/dichloromethane and 0.5% acetic acid in 6% methanol/dichloromethane as eluants to give 61.9 mg (50%) of pure Example 8.

TLC: silica gel, 0.75% acetic acid in 6% methanol/dichloromethane $R_f$ 0.48, iodine.

What is claimed is:

1. A compound of the formula

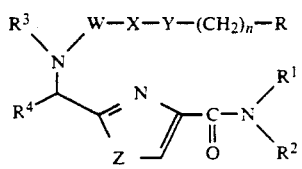

wherein

W is —(CH$_2$)$_m$— or

X is —(CH$_2$)$_2$—, —CH=CH— or phenylene;

Y is —O—, a single bond or —CH=CH—, except that Y cannot be —O— when n is 0, and if Y is vinylene, then n must be 0;

Z is O or NH;

m is 1, 2 or 3;

n is 0, 1, 2 or 3;

R is CO$_2$H, CO$_2$alkyl, CO$_2$alkali metal, CH$_2$OH, CONHSO$_2$R$^5$, CONHR$^6$, or —CH$_2$-5-tetrazolyl;

R$^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide, each of R$^1$ being unsubstituted or optionally substituted with alkyl, aryl, cycloalkyl, or cycloalkylalkyl;

R$^2$ is hydrogen, alkyl, aryl, or aralkyl; or

R$^1$ and R$^2$ together with the nitrogen to which they are linked form a 5- to 8-membered ring which contains only the single N heteroatom;

R$^3$ and R$^4$ together complete a pyrrolidinyl or imidazolyl ring, optionally substituted through a ring carbon atom with a halo, trifluoromethyl, oxo or hydroxyl group;

R$^5$ is alkyl, aryl or aralkyl; and

R$^6$ is hydrogen, alkyl, aryl or aralkyl; and wherein "cycloheteroalkyl" refers to 5-, 6- or 7-membered saturated rings that include 1 or 2 heteroatoms selected from nitrogen, oxygen and sulfur; and "heteroaryl" refers to 5- or 6-membered aromatic rings that include 1 or 2 heteroatoms selected from nitrogen, oxygen and sulfur.

2. The compound of claim 1 having the formula

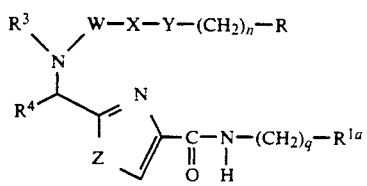

wherein q is an integer from 1 to 7 and R$^{1a}$ is cycloalkyl or aryl.

3. The compound of claim 1, wherein n is 2.

4. The compound of claim 1, wherein W is —(CH$_2$)$_m$— and m is 1.

5. The compound of claim 1, wherein R is CO$_2$H, CO$_2$alkyl, or CO$_2$alkali metal.

6. The compound of claim 1 wherein X is phenylene.

7. The compound of claim 2, wherein R$^{1a}$ is cyclohexyl.

8. A method of inhibiting platelet aggregation, which comprises administering to a mammalian host an effective amount of a compound as defined in claim 1.

9. A method of inhibiting bronocho-constriction associated with asthma, which comprises administering to a mammalian host an effective amount of a compound as defined in claim 1.

10. A method of improving post-ischemic myocardial function, which comprises administering to a mammalian host in need of such treatment an effective amount of a compound as defined in claim 1.

11. A method of preventing or reducing venous thrombosis, which comprises administering to a mammalian host in need of such treatment an effective amount of a compound as defined in claim 1.

12. A method of preventing or reducing platelet loss during extracorporeal circulation, which comprises administering to a mammalian host in need of such treatment an effective amount of a compound as defined in claim 1.

13. A method of reducing post-ischemic myocardial injury, which comprises administering to a mammalian host in need of such treatment an effect amount of a compound as defined in claim 1 an effective amount of a thrombolytic agent within 6 hours of a myocardial infarction.

14. A compound selected from the group consisting of:

2-[[2-[4-[[(4-Cyclohexylbutyl)amino]carbonyl]-2-oxazolyl]-1-pyrrolidinyl]methyl]benzenepropanoic acid;

(S)-2-[[2-[4-[[(4-Cyclohexylbutyl)amino]carbonyl]-2-oxazolyl]-1-pyrrolidinyl]methyl]benzenepropanoic acid, monolithium salt;

(R)-2-[[2-[4-[[(4-Cyclohexylbutyl)amino]carbonyl]-2-oxazolyl]-1-pyrrolidinyl]methyl]benzenepropanoic acid, monolithium salt;

2-[[5-[4-[[(4-Cyclohexylbutyl)amino]carbonyl]-2-oxazolyl]-1H-imidazol-1-yl]methyl]benzenepropanoic acid;

2-[[2-[4-[[(4-Cyclohexylbutyl)amino)carbonyl]-2-oxazolyl]-5-oxo-1-pyrrolidinyl]methyl]benzenepropanoic acid;

(S)-2-[[2-Oxo-5-[4-[[(2-phenylethyl)amino)carbonyl]-2-oxazolyl]-1-pyrrolidinyl]methyl]benzenepropanoic acid;

2-[[2-[4-[[(4-Cyclohexylbutyl)amino]carbonyl]-2-oxazolyl]-1-pyrrolidinyl]carbonyl]benzenepropanoic acid; and (2S-cis)-2-[[2-[4-[[[2-(4-Chlorophenyl)ethyl]amino]carbonyl]-2-oxazolyl]-4-hydroxy-1-pyrrolidinyl]carbonyl]benzenepropanoic acid.

* * * * *